United States Patent
Watanabe et al.

[11] Patent Number: 5,733,770
[45] Date of Patent: Mar. 31, 1998

[54] 5-AMINOLEVULINIC ACID PRODUCING MICROORGANISM AND PROCESS FOR PRODUCING 5-AMINOLEVULINIC ACID

[75] Inventors: Keitaro Watanabe; Seiji Nishikawa; Tohru Tanaka; Yasushi Hotta, all of Saitama, Japan

[73] Assignees: Cosmo Research Institute; Cosmo Oil Co., Ltd., both of Tokyo, Japan

[21] Appl. No.: 575,818

[22] Filed: Dec. 20, 1995

[30] Foreign Application Priority Data

Dec. 20, 1994 [JP] Japan ................................... 6-316251
Dec. 22, 1994 [JP] Japan ................................... 6-336046

[51] Int. Cl.$^6$ ............................. C12N 1/20; C12P 13/00
[52] U.S. Cl. ................................... 435/252.1; 435/128
[58] Field of Search ................................ 435/252.1, 128

[56] References Cited

PUBLICATIONS

Derwent Abs 96–288825/30 Hotta et al EP–718405 (Jun. 1996).
Derwent Abs 94–237577/29 CosmoSogoKKK JP06169758 (Jun. 1994).
Derwent Abs 95–362972/47 Cosmo Oil Co Ltd JP07246088 (Sep. 1995).
Derwent Abs 93–269037/34 Shimizu Const. Co Ltd JP05184376 (Jul. 1993).
Derwent Abs 94–205032/25 Cosmo Sogo KKK JP06141895 (May 1994).
Derwent Abs XRAM–C90–158292 Kubota Corp JP02261389 (Oct. 1990).
Derwent Abs 94–353758 Shimizu Const Co. Ltd. JP06277081 (Oct. 1994).

Primary Examiner—Herbert J. Lilling
Attorney, Agent, or Firm—Sughrue, Mion, Zinn, Macpeak & Seas, PLLC

[57] ABSTRACT

A microorganism that produces 5-aminolevulinic acid, wherein the microorganism has a 5-aminolevulinic acid dehydratase variant having a reduced inhibitor constant for a 5-aminolevulinic acid dehydratate inhibitor. A microorganism that produces 5-aminolevulinic acid, wherein the microorganism is a photosynthetic bacterium that produces 5-aminolevulinic acid without light irradiation. A progess for producing 5-aminolevulinic acid comprising the step of culturing a microorganism that produces 5-aminolevulinic acid in a culture medium under at least one condition selected from the group consisting of (a) less than 1 ppm of dissolved oxygen concentration in the culture medium, (b) from −180 to 50 mV of oxidation-reduction potential in the culture medium, and (c) from $5\times10^{-9}$ to $(K_rM-2\times10^{-8})$ (mol of $O_2$/ml·min·cell) of cellular respiration rate, wherein $K_rM$ represents the maximum cellular respiration rate when oxygen is supplied in an excess quantity.

4 Claims, No Drawings

5,733,770

5-AMINOLEVULINIC ACID PRODUCING MICROORGANISM AND PROCESS FOR PRODUCING 5-AMINOLEVULINIC ACID

FIELD OF THE INVENTION

The present invention relates to a microorganism which can produce 5-aminolevulinic acid (to be referred to as "ALA" hereinafter) in a high concentration. Furthermore, the present invention relates to a process by which ALA can be produced in a high yield by culturing an ALA-producing microorganism and regulating the oxygen supply.

BACKGROUND OF THE INVENTION

ALA is a compound which is broadly present in the biosphere and plays an important role in the living body as an intermediate of the pigment biosynthesis pathway for tetrapyrrole compounds (vitamin $B_{12}$, heme, and chlorophyll). Specifically, ALA is biologically synthesized from glycine and succinyl CoA by 5-aminolevulinic acid synthase or from glutamyl-tRNA by glutamyl-tRNA reductase and glutamate-1-semialdehydo mutase, and then metabolized by 5-aminolevulinic acid dehydratase (hereinafter referred to as "ALA dehydratase").

Also, ALA is an excellent herbicide, insecticide, plant growth regulator and plant photosynthesis enhancing agent, and is not toxic to living creatures and does not persist in the environment due to its high decomposition property (JP-A-61-502814, JP-A-2-138201; the term "JP-A" as used herein means an "unexamined published Japanese patent application").

However, due to high production cost, ALA cannot practically be applied as a herbicide, a plant growth regulator or a plant photosynthesis enhancing agent (CHEMICAL WEEK, Oct., 29, 1984).

Under such circumstances, a number of chemical synthesis methods have been examined (for example, JP-A-2-76841 and JP-A-2-261389), but fully satisfactory methods have not been developed yet.

On the other hand, attempts have been made to develop a method for the production of ALA using microorganisms. For example, methods in which the genus Propionibacterium, Methanobacterium or Methanosarcina is used have been proposed (for example, JP-A-5-184376), but they result in extremely low productivity which cannot satisfy the industrial requirement for ALA.

Another method in which the genus Rhodobacter is used (JP-A-6-141875) is more productive than the microbial methods discussed above, but synthesis of a significant quantity of pigments by photosynthetic bacteria, including the genus Rhodobacter, requires light irradiation, and thus production of ALA as a pigment precursor also requires sufficient light irradiation, which entails high cost and there are many problems to be resolved before this method may be realized.

In order to produce ALA by microorganisms such as the genera Rhodobacter, Propionibacterium, Methanobacterium, and Methanosarcina (in order to prevent ALA produced by microorganisms from its metabolism by ALA dehydratase in the living body), a method in which an ALA dehydratase inhibitor (e.g., levulinic acid, 4,6-dioxoheptanoic acid) is added has been developed (JP-A-6-277081).

In some cases, however, this method requires addition of the inhibitor in a large quantity, namely 3 times or more, or 500 times or more the amount of ALA produced.

Use of such a large quantity of ALA dehydratase inhibitor causes considerable inhibition of the growth and function of the microorganisms, in addition to increased production costs and difficulty in carrying out the separation and isolation steps.

Thus, great effort has been directed toward the development of a method to minimize the amount of ALA dehydratase inhibitor necessary for the increased production of ALA.

Also, in order to increase production of ALA, it is desirable to find a microorganism that can fully grow and maintain sufficient ALA synthesizing activity under conditions where metabolism of ALA by ALA dehydratase can be inhibited to a degree and also where the amount of a tetrapyrrole compound necessary to obtain energy can be minimized without preventing growth and function of the microorganism.

Particularly, when such a microorganism is a photosynthetic bacterium, the above description is industrially beneficial, because it means that the bacterium can fully grow and maintain sufficient ALA synthesizing activity, under a condition that does not require light irradiation (heterotrophism) and requiring bacteriochlorophyll light-harvesting pigment synthesized from a tetrapyrrole compound.

In consequence, a method has been proposed in which ALA is produced by culturing a mutant strain of a bacterium belonging to the genus Rhodobacter under a heterotrophic condition which does not require light irradiation (JP-A-4-333521); however, the productivity of this method was small in comparison with the method requiring light irradiation.

Oxygen is indispensable for the formation of energy when a microorganism is cultured under a heterotrophic condition which does not require light irradiation.

It is reported, however, that oxygen inhibits pigment synthesis of photosynthetic bacteria, especially purple non-sulfur bacteria, and also in activates ALA synthesizing enzyme (*Protein, Nucleic Acid and Enzyme*, 15(3): 195 (1970)).

SUMMARY OF THE INVENTION

Accordingly, an object of the present invention is to provide a microorganism that can produce a significant amount of ALA by the addition of a low concentration of an ALA dehydratase inhibitor.

Another object of the present invention is to provide a process by which bacterial culturing can be carried out under aerobic conditions and, particularly in the case of CR-520 (FERM BP- 5255) as the ALA-producing microorganism of the present invention, ALA can be produced with a high yield independent of light irradiation or non-irradiation.

These and other objects of the present invention have been achieved by a microorganism that produces ALA, which has an ALA dehydratase variant having a reduced inhibitor constant for an ALA dehydratase inhibitor.

Furthermore, these and other objects of the present invention have been achieved by a microorganism that produces ALA, which is a photosynthetic bacterium that produces ALA without light irradiation.

Moreover, these and other objects of the present invention have been achieved by a process for producing ALA, which comprises the step of culturing a microorganism that produces ALA in a culture medium under at least one of condition selected from the group consisting of (a) less than 1 ppm of dissolved oxygen concentration in the culture medium, (b) from −180 to 50 mV of oxidation-reduction potential in the culture medium, and (c) from $5\times10^{-9}$ to $(KrM-2\times10^{-8})$ (mol of $O_2$/ml·min·cell) of cellular respiration rate, wherein KrM represents the maximum cellular respiration rate when oxygen is supplied in an excess quantity.

DETAILED DESCRIPTION OF THE INVENTION

The inventors of the present invention have conducted extensive studies and found that (1) an effective method can be obtained by using a microorganism capable of producing an ALA dehydratase variant having reduced inhibitor constants against inhibitors, or another microorganism capable of producing another ALA dehydratase variant having not only the just described characteristic, but also an increased Michaelis constant of ALA dehydratase for ALA. The present inventors have succeeded in creating such a microorganism by mutation breeding.

Next, it was found that (2), since photosynthetic bacteria contain bacteriochlorophyll in a large quantity and therefore, are highly able to synthesize ALA, which is a precursor of the pigment, formation of a tetrapyrrole compound by metabolizing ALA can be reduced and, as a result, ALA can be produced in a large amount when such bacteria are converted into mutants that can grow even in the presence of a small amount of the tetrapyrrole compound as described above.

As a consequence, the inventors have found that a condition involving no light irradiation is effective in obtaining such a microorganism by mutation and selection; namely a condition under which a mutant strain having reduced photosynthesis capacity can grow and requires only a small amount of a tetrapyrrole compound. The present inventors have succeeded in creating such a microorganism.

In addition, it was confirmed (3) that microorganisms having the above characteristics (1) and (2) can produce a considerable amount of ALA by the addition of only an extremely low concentration of an ALA dehydratase inhibitor.

Furthermore, taking such situations into consideration, the inventors of the present invention have conducted extensive studies and found that a large amount of ALA can be produced without negatively affecting the amount of oxygen necessary for the formation of energy in bacterial cells when an ALA-producing photosynthetic bacterium is used and the oxygen supply is limited. The present invention has been accomplished on the basis of this finding.

A method for preparing the ALA-producing microorganism of the present invention and a process for producing ALA using the inventive microorganism are described in detail as follows.

First, the ALA-producing microorganism of the present invention is a mutant strain capable of producing an ALA dehydratase variant having a-reduced inhibitor constant for an ALA dehydratase inhibitor, which is obtained by using a strain belonging, for example, to the genus Rhodobacter, Rhodopseudomonas, Propionibacterium, Methanobacterium, Methanosarcina, Pseudomonas, Escherichia, Saccharomyces, Rhodospirillum, Rhodopila, Rhodomicrobium or Rhodocyclus or a mutant thereof as the parent strain and subjecting it to mutagenesis.

Preferably, the ALA-producing microorganism may produce an ALA dehydratase variant having not only the above characteristic, but also an increased Michaelis constant for ALA.

The following illustrates a method for the isolation of the ALA-producing microorganism of the present invention that has such properties.

A liquid medium in which the aforementioned parent strain can grow is prepared in a test tube and sterilized, and the parent strain is inoculated into the tube and cultured on a shaker. The thus grown cells are washed with a buffer solution and subjected to mutagenesis.

The mutagenesis can be effected in the usual way. For example, a physical mutagen, such as UV rays or ionizing radiation, may be applied to the parent strain on an agar medium, or the parent strain may be cultured in a buffer solution supplemented with a chemical alkylating agent mutagen, such as ethylmethane sulfonate (EMS), N-methyl-N'-nitro-N-nitrosoguanidine (NTG) or ethylnitrosourea (ENU), or a base analog mutagen, such as bromodeoxyuridine (BrdUrd).

The thus mutagen-treated cells are again washed with a buffer solution, spread on an agar medium and cultured.

Next, a strain having the aforementioned properties is selected from the mutant strains grown by this culturing process in the following manner.

Step 1: The mutant strains are grown in a medium for use in the culturing of a strain CR-520, which will be described later, and the resulting cells are collected, washed and disrupted in an appropriate buffer solution, and then centrifuged to remove undisrupted cells.

Step 2: The cell free extract obtained by the above step 1 is mixed with an ALA dehydratase reaction solution (cf. Example 1 described below) to cause an enzyme reaction.

Step 3: The enzyme reaction of step 2 is carried out under varied conditions, in which concentrations of the substrate ALA and an ALA dehydratase inhibitor (for example, levulinic acid) are optionally changed, and calculating the reaction rate under each condition.

Though not particularly limited, the reaction rate may be calculated by measuring the amount of porphobilinogen formed in accordance with Ehrlich colorimetric assay method (Ehrlich reaction) (*J. Biol. Chem.*, 219: 435 (1956)), and the total amount of porphyrin in accordance with the method of Satto (*J. Nutr. Sci. Vitaminol.*, 27: 439 (1981)), and then calculating the reaction rate based on the following formula.

$$v = \frac{(a+4b)}{t} \times \frac{1}{p}$$

v: enzyme reaction rate (U/mg protein);

a: amount of porphobilinogen in 1 ml of enzyme reaction solution (µmol);

b: amount of porphyrin in 1 ml of enzyme reaction solution (µmol); it becomes 4b because 1 molecule of porphyrin consists of 4 porphobilinogen molecules;

p: amount of protein in 1 ml of enzyme reaction solution (=1 mg);

t: reaction time (=60 minutes).

The Michaelis constant and the inhibitor constant are calculated from the thus calculated reaction rate under each concentration of ALA and ALA dehydratase inhibitor (for example, levulinic acid).

There are many methods to calculate these constants. The Michaelis constant may be calculated, for example, from the intersection point of the regression line and substrate concentration axis obtained by the so-called Lineweaver-Burk plot in which reciprocal numbers of the enzyme reaction rate and concentration of ALA are plotted (see *Enzyme Reaction Mechanisms*, translated by I. Tabuse, published by Tokyo University Press corresponding to E. Zeffren et al., *The Study of Enzyme Mechanisms*, published by John Wiley & Sons, Inc. (1973)).

This technique, known as the Lineweaver-Burk method, is generally used to calculate the Michaelis constant, and the calculated Michaelis constant (Km value) is frequently used to evaluate enzyme-substrate (ALA in this invention) affinity as one of the basic properties of an enzyme. In this case, an increase in the Km value can be regarded as a decrease in affinity.

The inhibitor constant may be calculated, for example, by the so-called Dixon plot, in which reciprocal numbers of the enzyme reaction rate and the concentration of the inhibitor are plotted (see for example *Enzyme Reaction Mechanism*, translated by I. Tabuse, published by Tokyo University Press).

In this method, regression lines obtained from varied concentrations of ALA cross at one point, and the inhibitor constant (Ki value) is calculated by multiplying the number corresponding to the inhibitor concentration axis at the intersection point by −1.

The affinity of enzymes and inhibitors can be evaluated using Ki values, and a decrease in Ki values generally means an increase in the affinity of inhibitors for enzymes.

The term "ALA dehydratase inhibitor" as used herein means all compounds which decrease the production rate of porphobilinogen when they are present in a reaction system in which ALA is converted into porphobilinogen by the action of ALA dehydratase. Such compounds include those which block the ALA binding site of ALA dehydratase and thereby inhibit association of ALA and ALA dehydratase, due to partial changes in the functional groups of ALA, which is the primary substrate of ALA dehydratase; or compounds having at least one structure selected from a similar molecular shape, similar van der Waals radius and other similar electronic states.

Examples of such compounds include at least one compound selected from the group consisting of levulinic acid, 5-chlorolevulinic acid, 5-bromolevulinic acid, 5-ketohexanoic acid, 2-methylsuccinic acid, 2-oxoadipic acid, acetic acid, succinamic acid, 3-oxoadipic acid, monomethyl succinate, 4-ketopimelic acid, and propionic acid.

As described in the foregoing, inhibition increases as the ratio of the Ki value to the Km value decreases.

The inhibitor constant and the Michaelis constant of the ALA dehydratase produced by the parent strain used in the mutagenesis are also measured in accordance with the aforementioned step 3, and these values are used as criteria for the selection of a mutant strain having a decreased Ki value and an increased Km value.

The parent strain to be used in obtaining such a mutant strain is optionally selected from the aforementioned microorganisms.

For example, wild strains of photosynthetic bacteria or mutant strains thereof may be used, but it is desirable to use a mutant strain capable of producing an ALA dehydratase variant already having a high Km value for ALA, such as *Rhodobacter sphaeroides* CR-386 or its variant CR-450.

However, when an ALA dehydratase of the thus obtained mutant strain has too large a Km value, growth of the mutant strain becomes extremely poor, which is in some cases due to the insufficient formation of porphobilinogen that required for its growth.

In consequence, it is desirable to use a mutant strain having a Km value of equal to or lower than 100 times the Km value of the wild strain.

In this instance, growth inhibition due to a large Michaelis constant is not necessary when the inhibition can be prevented by the addition of a nutrient source, such as porphobilinogen, to the culture medium.

In addition, a more efficient selection can be made by carrying out a preliminary selection based on the evaluation of ALA productivity, by making use of the Ehrlich method, prior to the aforementioned Km and Ki based selection.

*Rhodobacter sphaeroides* CR-520 is a preferred strain obtained by the above mutation/isolation procedure.

Next, the ALA-producing microorganism of the present invention that is a photosynthetic bacterium and that can grow without light irradiation and produce ALA (to be referred to as "ALA-producing photosynthetic microorganism" hereinafter) is obtained by using a photosynthetic bacterium such as a strain belonging to the genus Rhodobacter or a mutant strain thereof as the parent strain and subjecting it to mutagenesis.

The following illustrates a method for the isolation of the ALA-producing photosynthetic microorganism of the present invention having such properties.

A liquid medium in which the aforementioned parent strain can grow is prepared in a test tube and sterilized, and the parent strain is inoculated into the medium and cultured on a shaker. The thus grown cells are washed with a buffer solution and subjected to mutagenesis.

The mutagenesis is carried out in the usual way in the same manner as the case of the aforementioned mutation of ALA-producing microorganisms.

In order to select a strain having the aforementioned properties from the thus obtained mutant strains, these bacterial cells are cultured on a shaker without light irradiation (in the dark).

Thereafter, an efficient selection can be made by carrying out evaluation of ALA productivity, for example, by the Ehrlich method.

As a matter of course, a more efficient selection can be made by combining the aforementioned method for the selection of an ALA-producing microorganism and the just described method for the selection of an ALA-producing photosynthetic microorganism.

*Rhodobacter sphaeroides* CR-520 is a preferred strain obtained by the above mutation/isolation procedure.

As will be described later in Example 1, this strain is a mutant derived from *Rhodobacter sphaeroides* CR-450 by NTG treatment. It has almost the same bacteriological properties of the parent strain, with the exception that it has reduced photosynthetic ability, the Ki value for the ALA dehydratase inhibitor is decreased, the Km value for ALA is increased, it produces a considerable amount of ALA even without light irradiation, and its colonies are brown while those of the parent strain are red.

The strain CR-520 has been deposited in National Institute of Bioscience and Human Technology, Agency of Industrial Science and Technology, as Deposit No. FERM BP- 5255.

Production of ALA by CR-520 can be effected easily under commonly used microbial culture conditions, preferably by the following ALA production method of the present invention.

It is desirable to supplement the culture medium with assimilable carbon and nitrogen sources. As the carbon source, saccharides (e.g., glucose) and acids (e.g., acetic acid, malic acid, lactic acid, succinic acid) may be used. Examples of the nitrogen source include inorganic nitrogen sources, such as ammonia nitrogen compounds (e.g., ammonium sulfate, ammonium chloride) and nitrate nitrogen compounds (e.g., sodium nitrate), and organic nitrogen compounds, such as urea, polypeptone and yeast extract.

The culture medium may also contain trace components, such as inorganic salts; amino acids, such as alanine, valine, leucine, isoleucine, proline, phenylalanine, tryptophan, methionine, glycine, serine, threonine, cysteine, glutamine, asparagine, tyrosine, lysine, arginine, histidine, aspartic acid and glutamic acid; and natural components, such as yeast extract, dry yeast, peptone, meat extract, malt extract, corn steep liquor and casamino acid.

When ALA is produced, it is desirable to add at least one of glycine and levulinic acid to the medium. Glycine may be added in an amount preferably from 5 to 100 mM, more preferably from 10 to 60 mM; and levulinic acid in an amount preferably from 0.01 to 60 mM, more preferably from 0.1 to 30 mM. Since the addition of glycine and levulinic acid may sometimes cause reduced growth rate, they may be added after a certain period of strain growth.

Culturing may be carried out under such temperature and pH conditions that the strain can grow, namely at a temperature of from 10° to 40° C., preferably from 20° to 35° C.; and at a pH of from 4 to 9, preferably from 5 to 8.

When the medium pH changes during the production of ALA, it is desirable to adjust the pH level with an alkaline solution, such as sodium hydroxide, ammonia and potassium hydroxide, or with an acid, such as hydrochloric acid, sulfuric acid and phosphoric acid.

Although high yields of ALA may be produced in some cases when the strain is cultured under light irradiation, a large quantity of ALA can be obtained without light irradiation when the ALA-producing strain of the present invention, i.e., CR-520, is used.

Production of ALA can be carried out either simultaneously with the growth of cells or independently from cell growth. The microorganism to be used may be in the form of growing cells or resting cells, and these cells may be used as such for ALA production or may be used after increasing the cell density by collecting the cells by centrifugation and resuspending them in an appropriate solution, such as a medium or phosphate buffer.

According to the present invention, the oxygen supply is limited under at least one of the following conditions, in order to achieve efficient production of ALA as described in the foregoing:

(a) The dissolved oxygen concentration in the culture medium is usually limited to less than 1 ppm, preferably less than 0.5 ppm, more preferably less than 0.1 ppm (which is less than the detection limit of the currently available measuring instruments). This concentration can be measured using a dissolved oxygen meter.

(b) The oxidation-reduction potential in the culture medium is usually limited to from −180 to 50 mV, preferably from −100 to 20 mV, more preferably from −50 to 0 mV. This potential can be measured using an oxidation-reduction potentiometer.

(c) The cellular respiration rate is usually limited to from $5 \times 10^{-9}$ to (KrM$-2 \times 10^{-8}$) (mol of $O_2$/ml·min·cell), preferably from $1 \times 10^{-8}$ to (KrM$-4 \times 10^{-8}$) (mol of $O_2$/ml·min·cell).

In this case, KrM means the maximum cellular respiration rate when oxygen is supplied in an excess quantity, but it varies depending on each bacterium. For example, it is about $8 \times 10^{-8}$ mol of $O_2$/ml·min·cell in the case of *Rhodobacter sphaeroides* or *Rhodobacter capsulatus*. In consequence, the cellular respiration rate when such a bacterium is used becomes $5 \times 10^{-9}$ to $6 \times 10^{-8}$ (mol of $O_2$/ml·min·cell), preferably $1 \times 10^{-8}$ to $4 \times 10^{-8}$ (mol of $O_2$/ml·min·cell).

The cellular respiration rate can be measured using an exhaust oxygen/carbon dioxide analyzer.

Calculation of the cellular respiration rate was made using the following formula, which was obtained by dividing the general calculation expression of Hirose et al. (*Agric. Biol. Chem.*, 29: 931 (1965)) by the amount of cells, in order to correct the variation of the amount of cells per unit volume.

$$Rab/a = \frac{Q}{V} \cdot \frac{273}{273+T} \cdot \left[ \frac{100-(x_0+y_0)}{100-(x_1+y_1)} x_1 - x_0 \right] \cdot \frac{1}{100} \cdot \frac{1}{22.4} \cdot \frac{1}{10^3} \cdot \frac{1}{a}$$

Rab/a: cellular respiration rate (mol of $O_2$/ml·min·cell);
Q: aeration (ml/min);
V: medium volume (ml);
T: culture temperature (° C.);
$x_0$, $x_1$: oxygen concentration (%) at air outlet and inlet;
$y_0$, $Y_1$: COL concentration (%) at air outlet and inlet;
a: amount of cells, dry cell weight/l (cell).

The cellular respiration rate represents the oxygen absorption rate of cells in a culture vessel, and a large value indicates high use of oxygen.

At least one of these indexes (a) to (c) may be used, but it is desirable to analyze two or more of them, because they show a similar tendency in many cases.

Various means can be employed to satisfy these conditions, such as increasing and decreasing the aeration ratio, agitation speed and medium volume in the culture vessel; controlling the oxygen partial pressure in the aeration gas; adding a reducing compound; and regulating medium feeding.

Since oxygen supply is limited according to the present invention, strain growth rate is reduced in some cases. In that case, sufficient oxygen is supplied during the cells growing stage, and oxygen control is started after appropriate growth of the cells.

ALA in the thus obtained culture broth can be purified by commonly used means, such as ion exchange, chromatography and extraction.

Examples of microorganisms applicable to the process of the present invention include photosynthetic bacteria and purple non-sulfur bacteria capable of producing ALA, such as bacterial strains belonging to the genera Rhodobacter, Rhodopseudomonas, Propionibacterium, Methanobacterium, Methanosarcina, Pseudomonas, Escherichia, Saccharomyces, Rhodospirillum, Rhodopila, Rhodomicrobium and Rhodocyclus as well as their mutant strains. These microorganisms are disclosed, for example, in Bergey's Manual of Determinative Bacteriology, 3: 1658 (1989). According to the present invention, it is desirable to use a strain which produces as large an amount of ALA as possible under aerobic conditions or in a medium supplemented with natural components. *Rhodobacter sphaeroides* CR-520, which has been deposited in National Institute of Bioscience and Human-Technology, Agency of Industrial Science and Technology, as Deposit No. FERM BP- 5255, is an example of such a strain.

According to the microorganism of the present invention, which can produce an ALA dehydratase variant having a reduced Ki value for an ALA dehydratase inhibitor or further having an increased Km value for ALA, the ability to convert two molecules of ALA produced by the microorganism into porphobilinogen decreases considerably in a specific manner only by adding a trace amount of an ALA dehydratase inhibitor.

Because of this, production of ALA by the microorganism of the present invention can be achieved under a condition in which the ALA dehydratase inhibitor is added within such a range that it does not inhibit growth and activity of the microorganism, so that productivity of ALA is greatly increased.

In addition, according to the process of the present invention, ALA can be produced in a large amount from the ALA-producing microorganism.

Examples of the present invention are given below by way of illustration and not by way of limitation. Unless otherwise indicated, all parts, percents, ratios and the like are by weight.

EXAMPLES

Example 1

A glutamate-glucose medium (medium 1) shown in Table 1 was dispensed in 10 ml portions into test tubes having a diameter of 21 mm (21 mmφ test tubes), sterilized at 121° C. for minutes and then cooled spontaneously.

TABLE 1

|  | g/l (distilled water) |
|---|---|
| Sodium glutamate | 3.8 |
| Glucose | 9.0 |
| Dipotassium hydrogenphosphate | 0.5 |
| Potassium dihydrogenphosphate | 0.5 |
| Ammonium sulfate | 0.8 |
| Magnesium sulfate | 0.2 |
| Calcium chloride | 0.053 |
| Manganese sulfate | $1.2 \times 10^{-3}$ |
| Nicotinic acid | $1.0 \times 10^{-3}$ |
| Biotin | $1.0 \times 10^{-5}$ |
| Thiamin | $1.0 \times 10^{-3}$ |
| Yeast extract | 2.0 |

One loopful of strain CR-450 was inoculated into the thus prepared medium and cultured in the dark at 30° C. for 2 days on a shaker.

Medium 1 was dispensed in 10 ml portions into another 21 mmφ test tubes and sterilized in the same manner as described above. A 0.5 ml portion of the culture broth obtained above was inoculated into the thus prepared medium and cultured in the dark at 30° C. for 18 hours on a shaker.

The thus obtained culture broth was subjected to 5 minutes of centrifugation at 10,000 rpm, the resulting supernatant fluid was discarded, and the thus washed cells were suspended in the same volume of Tris-maleic acid buffer (pH 6.0). This washing step was conducted twice.

Thereafter, the cell suspension was again subjected to 5 minutes of centrifugation at 10,000 rpm, the resulting supernatant fluid was discarded, and then the thus obtained cells were suspended in Tris-maleic acid buffer (pH 6.0) containing 100 µg/ml of NTG and subjected to 80 minutes of standing culture at room temperature.

The thus mutagen-treated cells were washed three times in the same manner as described above and then inoculated into test tubes containing sterilized medium 1 and cultured in the dark at 30° C. for 2 days on a shaker.

Separately from this, agar was added to medium 1 in an amount of 15 g/l and sterilized at 121° C. for 15 minutes to prepare agar plates. The culture broth obtained above was diluted and spread on the agar plate and cultured in the dark at 30° C. for 4 days.

As the result, about 15,000 colonies were obtained.

Example 2

Sterilized medium 1 was dispensed in 0.2 ml portions into wells of sterile 96 well microplates, and about 15,000 colonies described above were separately inoculated into these wells.

After 24 hours of culturing in the dark at 30° C. on a microplate shaker, glycine and levulinic acid were added to each well to final concentrations of 30 mM and 1 mM, respectively.

After an additional 24 hours of shaking the culture under the same conditions described above, the culture broth in each well was collected and checked by the Ehrlich reaction to select 70 mutant strains showing high absorbance at 553 nm.

Example 3

Medium 1 (200 ml) was prepared in a 500 ml capacity shaking flask. This was sterilized at 121° C. for 15 minutes and then spontaneously cooled.

Each of mutant strains of CR-450 obtained in Example 2 was inoculated into a 21 mmφ test tube containing 10 ml of medium 1 which was sterilized in the same manner as described in the foregoing and cultured in the dark at 30° C. for 48 hours on a shaker.

The entire portion of the culture broth was inoculated into the aforementioned shaking flask and cultured in the dark at 30° C. for 48 hours on a shaker, and the resulting cells were collected by centrifugation.

The thus collected cells were washed with Tris-HCl buffer (40 mM, pH 8.1), suspended in 5 ml of the same buffer, disrupted using an ultrasonic disruption apparatus in the usual way and then subjected to 30 minutes of centrifugation at 10,000 rpm. The thus obtained supernatant fluid was used as a crude ALA dehydratase solution.

To 1 ml of Tris-HCl buffer (40 mM, pH 8.1) containing 33 mM of KCl and 6.5 mM of $MgCl_2$ was added the crude enzyme solution obtained above in an amount of 1.0 mg/ml in terms of protein, thereby preparing an enzyme reaction solution.

The thus prepared enzyme reaction solution was mixed with ALA (0.32, 0.65, 1.3, 3.2 or 6.5 mM) and levulinic acid (0, 0.01, 0.05, 0.2, 1.0 or 5.0 mM) and incubated at 37° C.

After 60 minutes of incubation, the reaction was stopped by adding 2 ml of 5% by volume trichloroacetic acid. This was centrifuged at 3,500 rpm for 10 minutes, and a 1 ml portion of the resulting supernatant fluid was checked by the aforementioned Ehrlich colorimetric determination method to examine the porphobilinogen content "a" formed in the reaction solution.

Another 1 ml portion of the supernatant fluid was checked by the aforementioned Satto method to examine total porphyrin content "b" in the reaction solution.

Using the aforementioned formula 1, the formation rate of porphobilinogen was calculated from these amounts "a" and "b" and used as the reaction rate of ALA dehydratase.

The reciprocal number of the reaction rate was plotted against the concentration of levulinic acid to obtain the regression line of each ALA concentration.

Since respective regression lines cross at one point, the inhibitor constant (i.e., Ki value) was obtained from the crossing point-corresponding value of the levulinic acid concentration axis.

Also, the reciprocal number of the reaction rate was plotted against the reciprocal number of ALA concentration to obtain a regression line, and the Michaelis constant (Km) was obtained from the crossing point of the regression line and the axis of the reciprocal ALA concentration.

Among the examined mutant strains, isolated strain CR-514 possessed an ALA dehydratase variant having a reduced Ki value for the ALA dehydratase inhibitor (levulinic acid) and was able to produce ALA; strain CR-520 possessed an ALA dehydratase variant having an increased Km value for ALA and a reduced Ki value for the ALA dehydratase inhibitor (levulinic acid) and was able to produce ALA by growing without light irradiation; and strain CR-533 produced a considerable amount of ALA even in the dark, in spite of unchanged Ki and Km values.

The Ki and Km values of strains CR-514, CR-520 and CR-533 are shown in Table 2.

Comparative Example 1

The process of Example 3 was conducted, except that *Rhodobacter sphaeroides* IFO 12203 was used to calculate Ki and Km values. The results are shown in Table 2.

Comparative Example 2

The process of Example 3 was conducted, except that *Rhodobacter sphaeroides* CR-450 was used to calculate Ki and Km values. The results are also shown in Table 2.

TABLE 2

|  | Ki | Km |
|---|---|---|
| Example 3 |  |  |
| CR-514 | 0.21 | 0.76 |
| CR-520 | 0.07 | 1.30 |
| CR-533 | 0.36 | 0.76 |
| Comparative Example 1 | 0.35 | 0.34 |
| Comparative Example 2 | 0.37 | 0.75 |

As is evident from the results shown in Table 2, the strain CR-520 possessed an ALA dehydratase variant having an increased Km value for ALA and a reduced Ki value for levulinic acid (an ALA dehydratase inhibitor).

Example 4

A 500 ml portion of medium 1 was prepared in a 2 l capacity shaking flask. This was sterilized at 121° C. for 15 minutes and then spontaneously cooled.

Separately from this, each of the mutant strains CR-514, CR-520 and CR-533 obtained in Example 3 was inoculated into a 21 mmφ test tube containing 10 ml of medium 1 which was sterilized in the same manner as described in the foregoing and cultured in the dark at 30° C. for 48 hours on a shaker.

The entire portion of each culture broth was inoculated into the aforementioned shaking flask and cultured in the dark at 30° C. for 48 hours on a shaker, and the resulting cells were collected by centrifugation.

The thus collected cells were suspended in 150 ml of sterilized medium 1, to a wet cell density of about 0.3 g/10 ml, and the cell suspension was mixed with 30 mM of glycine and dispensed in 10 ml portions into 21 mmφ test tubes. After adding varied concentration of levulinic acid, shaking culture was carried out at 30° C. in the dark.

The amount of ALA in the resulting culture broths was determined 15 and 30 hours thereafter in accordance with the method of Okayama et al. (*Clinical Chemistry*, 36(8): 1494 (1990)). The results are shown in Table 3.

Comparative Example 3

The process of Example 4 was conducted, except that *Rhodobacter sphaeroides* IFO 12203 was used and the amount of levulinic acid was changed as shown in Table 3. The amount of ALA in the culture broths after 15 and 30 hours of culturing was determined in the same manner as described in Example 4. The results are also shown in Table 3.

Comparative Example 4

The process of Example 4 was conducted, except that *Rhodobacter sphaeroides* CR-450 was used and the amount of levulinic acid was changed as shown in Table 3. The amount of ALA in the culture broths after 15 and 30 hours of culturing was determined in the same manner as described in Example 4. The results are shown in Table 3.

TABLE 3

|  | Concentration of levulinic acid (mM) | Amount of ALA formed after | |
|---|---|---|---|
|  |  | 15 hours (mM) | 30 hours (mM) |
| Example 4 |  |  |  |
| CR-514 | 1 | 1.5 | 1.5 |
|  | 5 | 2.0 | 3.0 |
|  | 10 | 2.2 | 4.1 |
| CR-520 | 0 | 0.4 | 0.2 |
|  | 0.5 | 2.0 | 2.8 |
|  | 1 | 2.5 | 4.5 |
|  | 5 | 3.0 | 6.5 |
| CR-533 | 5 | 1.7 | 2.4 |
|  | 15 | 2.4 | 3.9 |
|  | 30 | 2.2 | 3.3 |
| Comparative Example 3 | 5 | 0.01 | 0 |
|  | 15 | 0.1 | 0 |
| Comparative Example 4 | 0 | 0.2 | 0 |
|  | 5 | 1.5 | 1.5 |
|  | 15 | 2.5 | 3.8 |
|  | 30 | 2.0 | 2.5 |

As is evident from the results shown in Table 3, the strain CR-520 as an example of the microorganism of the present invention that can grow without light irradiation and have an ALA dehydratase variant having an increased Km value for ALA and a reduced Ki value for levulinic acid, such that the amount of levulinic acid necessary for its production can be reduced.

Example 5

One liter of medium 1 was put into a 2 liter capacity fermentation vessel, sterilized at 121° C. for 15 minutes and then cooled to room temperature.

Strain CR-520 (FERM BP- 5255), which was grown in advance by shaking culture under aerobic conditions using a 1 liter capacity Sakaguchi flask containing 200 ml of medium 1 (KrM=8.2×10$^{-8}$), was inoculated into the above fermenter to carry out aeration agitation culturing at 30° C. with an aeration rate of 0.1 v/v/m and an agitation speed of 200 rpm. All of the culturing steps were carried out without light irradiation. After 48 hours of culturing, the cell density was 0.64 g per 1 l medium.

Next, glycine, levulinic acid, glucose and yeast extract were added to the medium to final concentrations of 60 mM, 5 mM, 50 mM and 1%, respectively. The pH was corrected to pH 6.5 to 7.0 using 1 N sodium hydroxide and 1 N sulfuric acid.

The aeration rate was reduced to 0.014 v air/v/m and $N_2$ gas was supplied at a rate of 0.086 v/v/m. The agitation speed was controlled at 200 rpm.

Culturing continued for 84 hours under these conditions.

The maximum ALA accumulation, dissolved oxygen concentration after 48 hours, and average oxidation-reduction potential and average cellular respiration rate after 48 hours until 84 hours of culturing are shown in Table 4. In this case, the dissolved oxygen concentration was measured using a dissolved oxygen indicator M-1032 and an oxygen membrane electrode for fermentation use, manufactured by Able Co., Ltd.; the oxidation-reduction potential was measured using a digital ORP controller manufactured by Mituwa Biosystem Co., Ltd. and an ORP electrode, manufactured by Ingold Co., Ltd.; and the cellular respiration rate was measured using an exhaust gas analyzer WSMR-1400 LB, manufactured by Westron Corp.

Example 6

The procedure of Example 5 was conducted, except that the agitation speed after 48 hours was changed to 300 rpm.

The maximum ALA accumulation, dissolved oxygen concentration after 48 hours, and average oxidation-reduction potential and average cellular respiration rate after 48 hours until 84 hours of culturing are shown in Table 4.

Example 7

The procedure of Example 5 was conducted, except that the agitation speed after 48 hours was changed to 400 rpm.

The maximum ALA accumulation, dissolved oxygen concentration after 48 hours, and average oxidation-reduction potential and average cellular respiration rate after 48 hours until 84 hours of culturing are shown in Table 4.

Example 8

The procedure of Example 5 was conducted, except that the agitation speed after 48 hours was changed to 500 rpm.

The maximum ALA accumulation, dissolved oxygen concentration after 48 hours, and average oxidation-reduction potential and average cellular respiration rate after 48 hours until 84 hours of culturing are shown in Table 4.

Example 9

The procedure of Example 5 was conducted, except that the agitation speed after 48 hours was changed to 600 rpm.

The maximum ALA accumulation, dissolved oxygen concentration after 48 hours, and average oxidation-reduction potential and average cellular respiration rate after 48 hours until 84 hours of culturing are shown in Table 4.

Comparative Example 5

The procedure of Example 5 was conducted, except that the agitation speed and aeration rate after 48 hours were changed to 400 rpm and 0.5 v air/v/m, respectively.

The maximum ALA accumulation, dissolved oxygen concentration after 48 hours, and average oxidation-reduction potential and average cellular respiration rate after 48 hours until 84 hours of culturing are shown in Table 4.

TABLE 4

| | Maximum ALA accumulation (mM) | Dissolved oxygen concentration (ppm) | Average ORP * (mV) | Average CRR * (*) |
|---|---|---|---|---|
| Example 5 | 1.5 | N.D. (less than 0.1) | −121 | 1.1 |
| Example 6 | 3.2 | N.D. (less than 0.1) | −64 | 1.4 |
| Example 7 | 5.2 | N.D. (less than 0.1) | −31 | 1.8 |
| Example 8 | 14.3 | N.D. (less than 0.1) | −7 | 2.2 |
| Example 9 | 8.1 | N.D. (less than 0.1) | −2 | 3.3 |
| Comparative Example 5 | N.D. (less than 0.01) | 12 | 105 | 8.2 |

Note:
N.D.: Not detectable
ORP: oxidation-reduction potential
CRR: cellular respiration rate ($\times 10^{-8}$ mol of $O_2$/ml · min · cell)

Example 10

The procedure of Example 5 was conducted, except that the strain was changed to *Rhodobacter capsulatus* ATCC 11166 (KrM=$8.5 \times 10^{-8}$) and the agitation speed after 48 hours was changed to 400 rpm.

The maximum ALA accumulation by this culture procedure was 0.086 mM, dissolved oxygen concentration in the medium after 48 hours of culturing was not detectable (less than 0.1 ppm), the average oxidation-reduction potential after 48 hours until 84 hours was −31 mV, and the average cellular respiration rate after 48 hours until 84 hours was $2.7 \times 10^{-8}$ (mol of $O_2$/ml·min·cell).

Comparative Example 6

The procedure of Comparative Example 5 was conducted, except that the strain was changed to *Rhodobacter capsulatus* ATCC 11166.

ALA accumulation by this culture procedure was not detectable (less than 0.01 mM), the dissolved oxygen concentration in the medium after 48 hours of culturing was 8 ppm, the average oxidation-reduction potential after 48 hours until 84 hours was 131 mV, and the average cellular respiration rate after 48 hours until 84 hours was $8.5 \times 10^{-8}$ (mol of $O_2$/ml·min·cell).

Example 11

Medium 1 (18 was put into a 30 liter capacity fermentation vessel and sterilized at 121° C. for 30 minutes.

Strain CR-520 (FERM BP- 5255) which was grown in advance by shaking culture under aerobic conditions using a 1 liter capacity Sakaguchi flask containing 200 ml of medium 1 was inoculated into the above fermenter to carry out aeration agitation culturing at 30° C. with an aeration rate of 0.1 v/v/m and an agitation speed of 200 rpm. All of the culturing steps were carried out in the dark. After 48 hours of the culturing, the cell density was 0.68 g per 1 l medium.

Next, glycine, levulinic acid, glucose and yeast extract were added to the medium to final concentrations of 60 mM, 5 mM, 50 mM and 1%, respectively, and the pH was corrected to pH 6.5 to 7.0 using 1 N sodium hydroxide and 1 N sulfuric acid.

The aeration rate was reduced to 0.028 v air/v/m and $N_2$ gas was supplied at a rate of 0.172 v/v/m. The agitation speed was controlled at 300 rpm.

Culturing continued until 84 hours under these conditions.

The maximum ALA accumulation by this culture procedure was 12.8 mM, dissolved oxygen concentration in the medium after 48 hours of culturing was not detectable (less than 0.1 ppm), the average oxidation-reduction potential after 48 hours until 84 hours was −22 mV, and the average cellular respiration rate after 48 hours until 84 hours was $2.2 \times 10^{-8}$ (mol of $O_2$/ml·min·cell).

While the invention has been described in detail and with reference to specific embodiments thereof, it will be apparent to one skilled in the art that various changes and modifications can be made therein without departing from the spirit and scope thereof.

What is claimed is:

1. A microorganism that produces 5-aminolevulinic acid, wherein the microorganism has a 5-aminolevulinic acid dehydratase variant having a reduced inhibitor constant for a 5-aminolevulinic acid dehydratase inhibitor, wherein the microorganism is selected from the group of genus Rhodobacter and mutant strains thereof.

2. The microorganism as claimed in claim 1, wherein the 5-aminolevulinic acid dehydratase variant has an increased Michaelis constant for 5-aminolevulinic acid.

3. A microorganism that produces 5-aminolevulinic acid, wherein the microorganism is a photosynthetic bacterium that produces 5-aminolevulinic acid without light irradiation, wherein the microorganism is selected from the group of genus Rhodobacter and mutant strains thereof.

4. A microorganism that produces 5-aminolevulinic acid, wherein the microorganism is *Rhodobacter sphaeroides* CR-520 under Deposit No. FERM BP- 5255.

* * * * *